(12) United States Patent
Yamazaki et al.

(10) Patent No.: US 7,538,242 B2
(45) Date of Patent: May 26, 2009

(54) OPTICALLY ACTIVE PPAR-ACTIVATING COMPOUND INTERMEDIATE AND METHOD FOR PRODUCING SAME

(75) Inventors: Yukiyoshi Yamazaki, Higashimurayama (JP); Takaaki Araki, Higashimurayama (JP); Minoru Koura, Kawagoe (JP); Kimiyuki Shibuya, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 59 days.

(21) Appl. No.: 11/816,921

(22) PCT Filed: Feb. 28, 2006

(86) PCT No.: PCT/JP2006/303741

§ 371 (c)(1),
(2), (4) Date: Aug. 23, 2007

(87) PCT Pub. No.: WO2006/093142

PCT Pub. Date: Sep. 8, 2006

(65) Prior Publication Data

US 2009/0023944 A1 Jan. 22, 2009

(30) Foreign Application Priority Data

Mar. 1, 2005 (JP) ............................. 2005-055686

(51) Int. Cl.
*C07C 69/76* (2006.01)
(52) U.S. Cl. ....................................................... 560/61
(58) Field of Classification Search ....................... None
See application file for complete search history.

(56) References Cited

U.S. PATENT DOCUMENTS

| | | | |
|---|---|---|---|
| 7,109,226 B2 | 9/2006 | Yamazaki et al. | |
| 7,183,195 B2 | 2/2007 | Yamazaki et al. | |
| 7,183,295 B2 | 2/2007 | Yamazaki et al. | |
| 7,186,746 B2 * | 3/2007 | Acton et al. ............... | 514/419 |

FOREIGN PATENT DOCUMENTS

| | | |
|---|---|---|
| JP | 53 71071 | 6/1978 |
| WO | 2004 020408 | 3/2004 |
| WO | 2004 020409 | 3/2004 |
| WO | 2005 023777 | 3/2005 |

OTHER PUBLICATIONS

Isabelle Issemann, et al. "Activation of a member of the steroid hormone receptor superfamily by peroxisome proliferators", Nature, vol. 347, Oct. 18, 1990, pp. 645-650.
Christine Dreyer, et al., "Control of the Peroxisomal β-Oxidation Pathway by a Novel Family of Nuclear Hormone Receptors", Cell, vol. 68, Mar. 6, 1992, pp. 879-887.
"A Unified Nomenclature System for the Nuclear Receptor Superfamily", Letter to the Editor, Cell, vol. 97, Apr. 16, 1999, pp. 161-163.
Kristina Schoonjans, et al., "The peroxisome proliferator activated receptors (PPARs) and their effects on lipid metabolism and adipocyte differentiation" Biochimica et Biophysica Acta 1302, 1996, pp. 93-109.
Timothy M. Willson, et al., "The PPARs: From Orphan Receptors to Drug Discovery", Journal of Medicinal Chemistry, vol. 43, No. 4, Feb. 24, 2000, pp. 527-550.
Frank J. Gonzalez, et al., "Mechanism of Action of the Nongenotoxic Peroxisome Proliferators: Role of the Peroxisome Proliferator-Activated Receptor α", Journal of the National Cancer Institute, vol. 90, No. 22, Nov. 18, 1998, pp. 1702-1709.
Jean-Charles Fruchart, et al., "Peroxisome proliferator-activated receptor-alpha activators regulate genes governing lipoprotein metabolism, vascular inflammation and atherosclerosis", Current Opinion in Lipidology, 1999,10, pp. 245-257.
Johan Auwerx, et al., "Regulation of Triglyceride Metabolism by PPARs: Fibrates and Thiazolidinediones have Distinct Effects", Journal of Atherosclerosis and Thrombosis, vol. 3, No. 2, Oct. 17, 1996, pp. 81-89.
Bart Staels, et al., "Role of PPAR in the Pharmalogical Regulation of Lipoprotein Metabolism by Fibrates and Thiazolidinediones", Current Pharmaceutical Design, 3, 1997, pp. 1-14.
Ines Pineda, et al., "Peroxisome proliferator-activated receptor alpha in metabolic disease, inflammation, atherosclerosis and aging", Current Opinion in Lipidology, 10, 1999, pp. 151-159.
Joseph Vamecq, et al., "Medical significance of peroxisome proliferator-activated receptors", The Lancet, vol. 354, Jul. 10, 1999, pp. 141-148.
Sander J. Robins, "PPARα ligands and clinical trials: cardiovascular risk reduction with fibrates", Journal of Cardiovascular Risk, 8, 2001, pp. 195-201.
The Lancet ,vol. 349, Mar. 29, 1997,p. 952.
Jennifer L. Oberfield, et al., "A peroxisome proliferator-activated receptor γ ligand inhibits adipocyte differentiation", Proc. Natl. Acad. Sci. USA, Biochemistry, vol. 96, May 1999, pp. 6102-6106.
Harold M. Wright, et al., "A Synthetic Antagonist for the Peroxisome Proliferator-activated Receptor γ inhibits Adipocyte Differentiation", The Journal of Biological Chemistry, Jan. 21, 2000, pp. 1873-1877.
Toshimasa Yamauchi, et al., "Inhibition of RXR and PPARγ ameliorates diet-induced obesity and type 2 diabetes", The Journal of Clinical Investigation, vol. 108, No. 7, Oct. 2001, pp. 1001-1013.
Yaacov Barak, et al., "Effects of peroxisome proliferator-activated receptor δ on the placentation, adiposity, and colorectal cancer", Proc. Natl. Acad. Sci., vol. 99, No. 1, Jan. 8, 2002, pp. 303-308.
U.S. Appl. No. 11/816,472, filed Aug. 16, 2007, Yamazaki, et al.
U.S. Appl. No. 11/816,921, filed Aug. 23, 2007, Yamazaki, et al.

* cited by examiner

*Primary Examiner*—Paul A Zucker
(74) *Attorney, Agent, or Firm*—Oblon, Spivak, McClelland, Maier & Neustadt, P.C.

(57) ABSTRACT

The present invention provides a production intermediate for compound (A-1) and a method for producing the intermediate at high yield and high optical yield.

2 Claims, No Drawings

OPTICALLY ACTIVE PPAR-ACTIVATING COMPOUND INTERMEDIATE AND METHOD FOR PRODUCING SAME

TECHNICAL FIELD

The present invention relates to a production intermediate for a compound which activates PPARs (peroxisome proliferator-activated receptors) and which is useful as a drug for preventing and/or treating diseases including hyperlipidemia, arteriosclerosis, and diabetes. The invention also relates to a method for producing the intermediate.

BACKGROUND ART

PPARs are known to be a family of nuclear receptors, and three sub-types thereof (α, γ, δ) have already been identified (Non-Patent Documents 1 to 5). Among the three sub-types, PPARα is expressed mainly in the liver and is known to be activated by a plasticizer or a fibrate-type drug such as Wy 14643 or a commercially available pharmaceutical; e.g., clofibrate, fenofibrate, bezafibrate, or gemfibrozil (Non-Patent Documents 6 and 7).

In mammals, activation of PPARα is known to promote β oxidation of fatty acids and to lower blood triglyceride level, and in humans, blood lipid levels such as low-density lipoprotein (LDL) cholesterol level and very low-density lipoprotein (VLDL) cholesterol level are known to decrease. Thus, a PPARα-activating agent is considered a useful drug for preventing and/or treating diseases such as hyperlipidemia. In addition, the PPARα-activating agent, which increases high-density lipoprotein (HDL) cholesterol level and, in blood vessels, suppresses expression of VCAM-1 (a type of cell adhesion factor), is considered to be useful for preventing and/or treating diseases such as arteriosclerosis, and for preventing and/or treating diseases such as diabetes, inflammatory disease, and heart diseases (Non-Patent Documents 8 to 14).

Activation of PPARγ in humans has been reported to cause adverse effects of increasing the amount of fat and body weight and causing obesity (Non-Patent Document 15). Recent studies have reported that a PPARγ antagonist also possibly improves insulin resistance (Non-Patent Documents 16 to 18). A document reports that activation of PPARδ causes lipid accumulation (Non-Patent Document 19). Therefore, a PPARα-selective activator having low activation property with respect to PPARγ and to PPARδ is promised to be useful for prevention and/or treatment, without accompanying obesity or increase in body weight, of pathological conditions including hyperlipidemia, arteriosclerosis, diabetes, complications of diabetes, inflammation, and heart diseases.

Under such circumstances, the present inventors previously found that compounds represented by formula (A):

[F1]

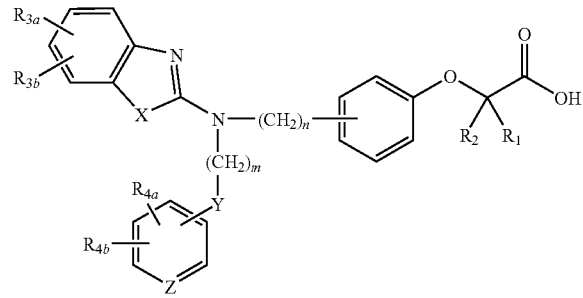

(A)

(wherein $R_1$ and $R_2$, which may be identical to or different from each other, each represent a hydrogen atom, a methyl group, or an ethyl group; $R_{3a}$, $R_{3b}$, $R_{4a}$, and $R_{4b}$, which may be identical to or different from one another, each represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group; linkage of $R_{3a}$ and $R_{3b}$, or linkage of $R_{4a}$ and $R_{4b}$ forms an alkylenedioxy group; X represents an oxygen atom, a sulfur atom, or N—$R_5$ (wherein $R_5$ represents a hydrogen atom, a $C_{1-4}$ alkyl group, a $C_{1-4}$ alkylsulfonyl group, or a $C_{1-4}$ alkyloxycarbonyl group); Y represents an oxygen group, an $S(O)_l$ group (wherein l is an integer of 0 to 2), a carbonyl group, a carbonylamino group, an aminocarbonyl group, a sulfonylamino group, an aminosulfonyl group, or an NH group; Z represents CH or N; n is an integer of 1 to 6; and m is an integer of 2 to 6) and salts thereof selectively activate PPARα, and therefore being useful as a drug, and filed a patent application (Patent Document 1).

Patent Document 1: WO 05/023777 pamphlet

Non-Patent Document 1: Nature, 347, 645-650, 1990

Non-Patent Document 2: Cell, 68, pp. 879-887, 1992

Non-Patent Document 3: Cell, 97, pp. 161-163, 1999

Non-Patent Document 4: Biochim. Biophys. Acta., 1302, pp. 93-109, 1996

Non-Patent Document 5: Journal of Medicinal Chemistry, 43, pp. 527-550, 2000

Non-Patent Document 6: Journal of the National Cancer Institute, 90, 1702-1709, 1998

Non-Patent Document 7: Current Opinion in Lipidology, 10, pp. 245-257, 1999

Non-Patent Document 8: Journal of Atherosclerosis and Thrombosis, 3, pp. 81-89, 1996

Non-Patent Document 9: Current Pharmaceutical Design, 3, pp. 1-14, 1997

Non-Patent Document 10: Current Opinion in Lipidology, 10, pp. 151-159, 1999

Non-Patent Document 11: Current Opinion in Lipidology, 10, pp. 245-257, 1999

Non-Patent Document 12: The Lancet, 354, pp. 141-148, 1999

Non-Patent Document 13: Journal of Medicinal Chemistry, 43, pp. 527-550, 2000

Non-Patent Document 14: Journal of Cardiovascular Risk, 8, pp. 195-201, 2001

Non-Patent Document 15: The Lancet, 349, pp. 952, 1997

Non-Patent Document 16: Proc. Natl. Acad. Sci., 96, pp. 6102-6106, 1999

Non-Patent Document 17: The Journal of Biological Chemistry, 275, pp. 1873-1877, 2000

Non-Patent Document 18: J. Clin. Invest., 108, 1001-1013, 2001

Non-Patent Document 19: Proc. Natl. Acad. Sci., 99, pp. 303-308, 2002

DISCLOSURE OF THE INVENTION

Problems to be Solved by the Invention

An object of the present invention is to provide a production intermediate for (R)-2-[3-[[N-(benzoxazol-2-yl)-N-3-

(4-methoxyphenoxy)propyl]aminomethyl]phenoxy]butyric acid (compound (A-1)), which is one of the compounds represented by formula (A). Another object of the invention is to provide a method for producing the intermediate at high yield and high optical yield.

Means for Solving the Problems

The present inventors have conducted extensive studies in order to provide a useful method for producing the aforementioned compound (A-1), and have found that, as shown in the following reaction scheme (I):

[F2]

Reaction scheme (I)

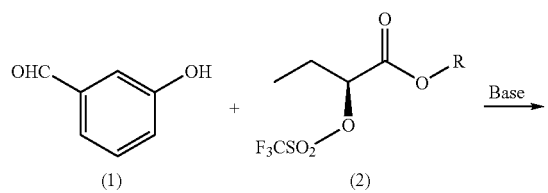

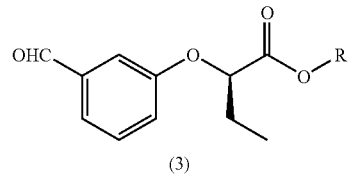

(wherein R represents a C1 to C6 alkyl group or a C7 to C8 aralkyl group), an optically active benzaldehyde derivative (compound (3)) can be produced at high yield and high optical purity through reaction between an optically active 2-trifluoromethanesulfonyloxybutyric acid ester (compound (2)) and 3-hydroxybenzaldehyde (compound (1)) in the presence of a base. The inventors have also found that, through a synthesis route via compound (3) (see the following reaction scheme (II) and Referential Examples described hereinbelow), compound (A-1) can be produced without decreasing yield and optical purity, and thus compound (3) can be a useful synthesis intermediate for compound (A-1):

[F3]

Reaction scheme (II)

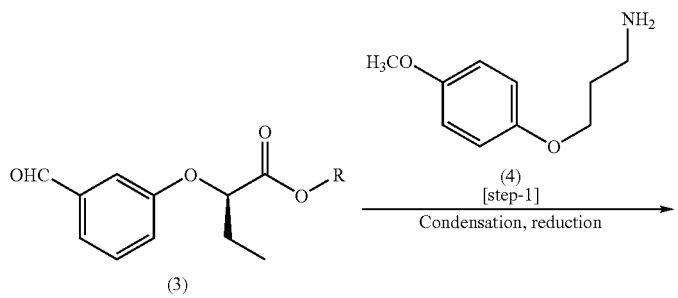

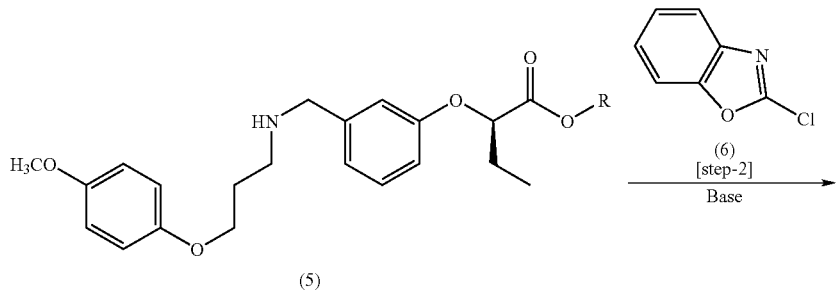

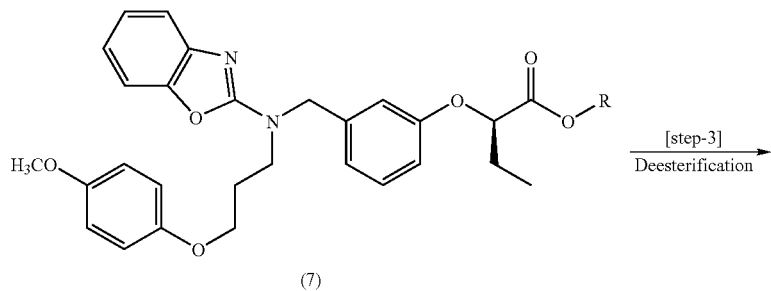

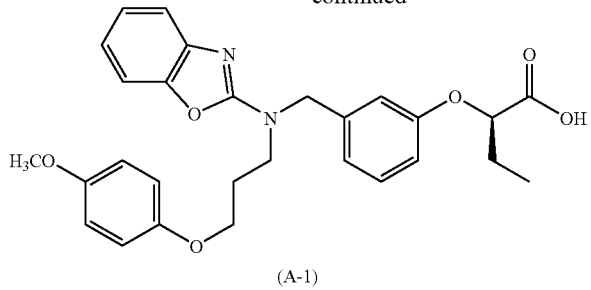

(A-1)

(wherein R has the same meaning as defined above).

Accordingly, the present invention is directed to a method for producing an optically active benzaldehyde derivative (compound (3)), characterized in that the method comprises reacting 3-hydroxybenzaldehyde (compound (1)) with an optically active 2-trifluoromethanesulfonyloxybutyric acid ester (compound (2)) in the presence of a base.

The present invention is also directed to an optically active benzaldehyde derivative (compound (3)).

Effects of the Invention

According to the method of the present invention, there can be provided, at high yield and high optical purity, a useful production intermediate for (R)-2-[3-[[N-(benzoxazol-2-yl)-N-3-(4-methoxyphenoxy)propyl]aminomethyl]phenoxy]butyric acid (compound (A-1)), which is a PPARα-selective activator and attains prevention and/or treatment, without accompanying obesity or increase in body weight, of pathological conditions including hyperlipidemia, arteriosclerosis, diabetes, complications of diabetes, inflammation, and heart diseases.

BEST MODES FOR CARRYING OUT THE INVENTION

According to the production method of the present invention, compound (1) is reacted with an optically active compound (2) in the presence of a base, to thereby produce a compound (3).

In the compounds (2) and (3), R represents a C1 to C6 alkyl group or a C7 to C8 aralkyl group. Examples of preferred alkyl groups include methyl, ethyl, n-propyl, isopropyl, n-butyl, isobutyl, and t-butyl, and examples of preferred aralkyl groups include benzyl and phenethyl.

The base employed in the reaction may be an inorganic base or an organic base. Examples of the inorganic base include alkali metal hydroxides such as lithium hydroxide, sodium hydroxide, and potassium hydroxide; alkali metal carbonates such as sodium carbonate, potassium carbonate, and cesium carbonate; alkali metal hydrogencarbonates such as sodium hydrogencarbonate and potassium hydrogencarbonate. Examples of the organic base include pyridine, triethylamine, N,N-diisopropylethylamine, N-methylmorpholine, and N,N-dimethylaniline. Of these, potassium carbonate is preferably used from the viewpoint of chemical yield.

The reaction is preferably performed in a solvent. No particular limitation is imposed on the type of solvent, and examples include halohydrocarbons such as methylene chloride, chloroform, carbon tetrachloride, 1,2-dichloroethane, and chlorobenzene; aromatic hydrocarbons such as benzene and toluene; ethers such as tetrahydrofuran, diethyl ether, and dioxane; ketones such as acetone and methyl ethyl ketone; aprotic polar solvents such as acetonitrile, N,N-dimethylformamide, and dimethyl sulfoxide; and ethyl acetate. Of these, acetonitrile is preferred.

The reaction is performed at 0 to 100° C. for 0.5 to 48 hours, preferably at 20 to 90° C. for 1 to 24 hours.

Patent Document 1 discloses transformation of a 2-hydroxycarboxylic acid ester to the corresponding phenyl ether form. In this process, the hydroxyl group of the 2-hydroxycarboxylic acid ester is converted (e.g., mesylated or tosylated) to a leaving group such as a methanesulfonyloxy group or a p-toluenesulfonyloxy group, and the modified ester form is reacted with a phenol compound in the presence of an inorganic base such as sodium carbonate, potassium carbonate, or cesium carbonate or an organic base such as triethylamine or N,N-diisopropylethylamine (reaction step: F-4). Patent Document 1 also discloses transformation of a 2-halocarboxylic acid ester to the corresponding phenyl ether form. In this process, the 2-halocarboxylic acid ester is reacted with a phenol compound in the presence of an inorganic base such as sodium carbonate, potassium carbonate, or cesium carbonate or an organic base such as triethylamine or N,N-diisopropylethylamine (reaction step: A-1). According to the method of the present invention, which differs from these reaction steps and which employs an optically active 2-trifluoromethanesulfonyloxybutyric acid ester (compound (2)), which has a trifluoromethanesulfonyloxy group as a leaving group, compound (3) can be produced at remarkably high yield and high optical purity (see the Examples described hereinbelow). Thus, the compound (3) is a useful production intermediate for compound (A-1).

The compound (2) may be synthesized through, for example, the following reaction scheme:

[F4]

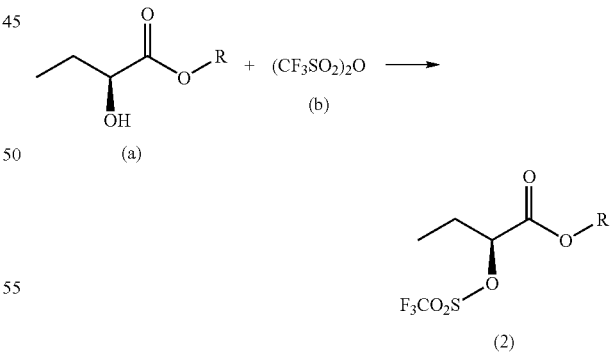

(wherein R has the same meaning as defined above), in which a (S)-2-hydroxybutyric acid ester (a) is reacted with trifluoromethanesulfonic anhydride (b) in a solvent such as methylene chloride, chloroform, carbon tetrachloride, 1,2-dichloroethane, toluene, or hexane, at −80 to 30° C. for 10 minutes to 3 hours.

The method for producing compound (A-1) employing the thus-produced compound (3) will next be described with reference to the following reaction scheme (II):

[F5]

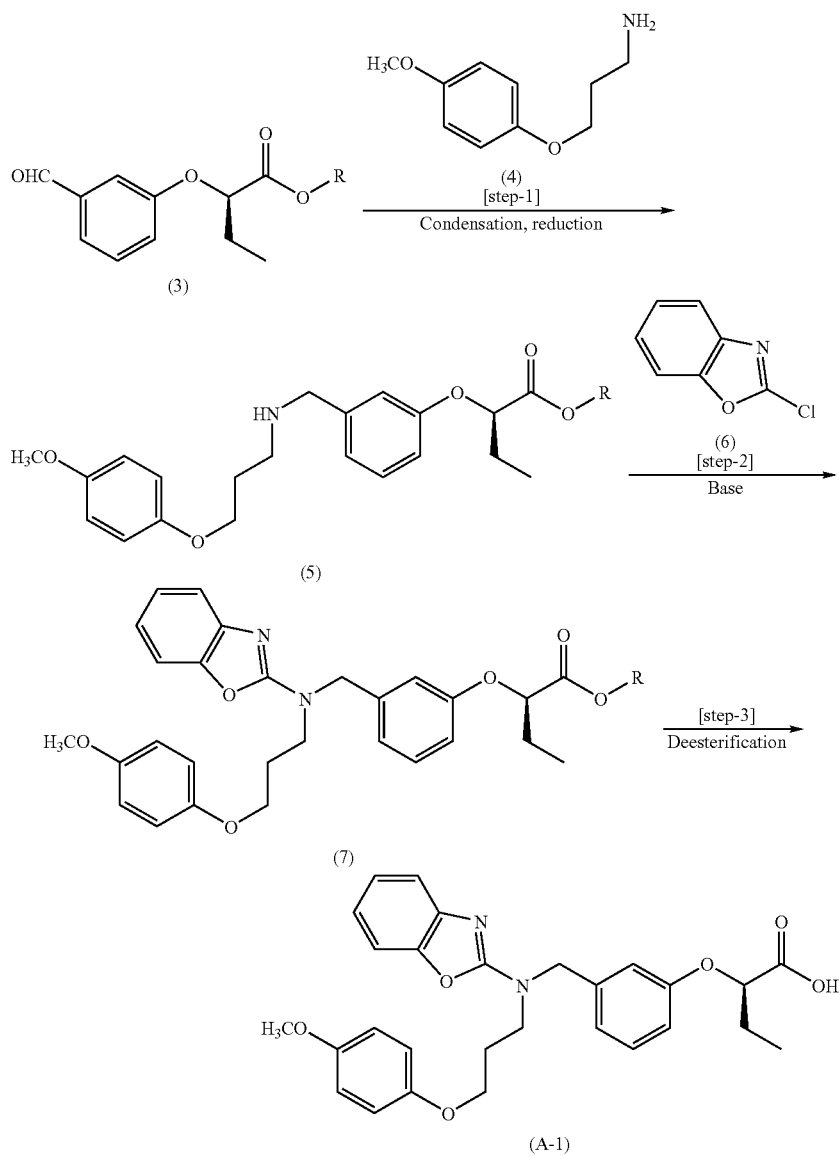

(wherein R has the same meaning as defined above).

[Step-1]

In step 1, an imino form or an iminium salt produced through condensation between a compound (3) and compound (4) is reduced, to thereby form an amine compound (5).

The condensation reaction between the compound (3) and compound (4) is performed in a solvent such as methanol, ethanol, isopropyl alcohol, tetrahydrofuran, dioxane, toluene, acetonitrile, or N,N-dimethylformamide, in the presence or absence of an acid such as acetic acid or hydrochloric acid. Generally, the reaction is performed at 20 to 100° C. for 1 to 12 hours.

Preferably, reduction is carried out by use of a hydrogenating/reducing agent such as sodium borohydride, sodium triacetoxyborohydride, or sodium cyanoborohydride in a solvent, for example, water, an alcohol (e.g., methanol, ethanol, or isopropyl alcohol), an ether (e.g., tetrahydrofuran, dioxane, or diethyl ether), a halohydrocarbon (e.g., dichloromethane or chloroform), acetonitrile, or dimethylformamide. In general, the reaction is preferably performed at 0 to 30° C. for about 1 to about 12 hours.

In step-2, the compound (5) is reacted with 2-chlorobenzoxazol (6) in the presence of a base, to thereby produce a compound (7).

The above reaction between the compound (5) and 2-chlorobenzoxazol (6) may be performed in a solvent, for example, N,N-dimethylformamide, acetonitrile, tetrahydrofuran, dioxane, chloroform, or ethyl acetate, at 20 to 100° C. for 1 to 12 hours.

Examples of the base employed in the reaction include inorganic bases such as sodium carbonate, potassium carbonate, and cesium carbonate; and organic bases such as triethylamine, N,N-diisopropylethylamine, and pyridine.

[Step-3]

In step 3, the ester moiety of the compound (7) is removed; i.e., the compound (7) is de-esterified, to thereby produce compound (A-1).

De-esterification may be performed through a conventional method such as hydrolysis or hydrogenolysis (reduction). Hydrolysis may be performed under any of reaction conditions employed for hydrolysis of ester. For example, the hydrolysis is performed in a solvent such as an alcohol (e.g., water, methanol, ethanol, or propanol), an ether (e.g., tetrahydrofuran or dioxane), a ketone (e.g., acetone or methyl ethyl ketone), or acetic acid, or a solvent mixture thereof, in the presence of an inorganic base such as lithium hydroxide, sodium hydroxide, potassium hydroxide, sodium carbonate, or potassium carbonate; a mineral acid such as hydrochloric acid, sulfuric acid, or hydrobromic acid; or an organic acid such as p-toluenesulfonic acid.

Generally, the reaction is performed at 0 to 100° C. for 0.5 to 24 hours, preferably at 10 to 50° C. for 1 to 12 hours.

In an exemplary embodiment of hydrogenolysis, the reaction is performed in an inert solvent such as an ether (e.g., tetrahydrofuran or dioxane), an ester (e.g., methyl acetate, ethyl acetate, or isopropyl acetate), an alcohol (e.g., methanol, ethanol, or isopropyl alcohol), or an amide (e.g., N,N-dimethylformamide), in the presence of a hydrogenation catalyst such as palladium-carbon, palladium black, palladium, palladium hydroxide, platinum-carbon, platinum dioxide, or Raney nickel), in the presence or absence of an inorganic acid such as hydrochloric acid, sulfuric acid, hypochlorous acid or an organic acid such as acetic acid, trifluoroacetic acid, or formic acid, and in a pressurized or non-pressurized hydrogen atmosphere.

Generally, the reaction is performed at 0 to 30° C. for 5 minutes to 24 hours, preferably at 10 to 25° C. for 1 to 12 hours.

The compound (4) may be synthesized through, for example, the following procedure.

[F6]

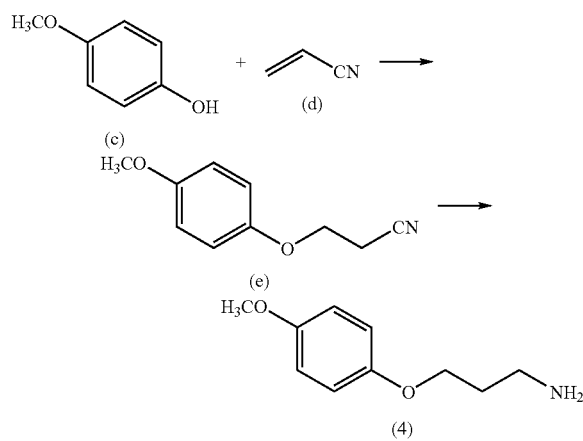

Specifically, 4-methoxyphenol (c) is reacted with acrylonitrile (d) in the presence of a base such as Triton B, triethylamine, or N,N-diisopropylethylamine, to thereby form 3-(4-methoxyphenoxy)propionitrile (e). The compound (e) is reduced by use of borane-tetrahydrofuran complex, borane-dimethyl sulfide complex, aluminum lithium hydride, or a similar compound, in a solvent such as tetrahydrofuran or dioxane, or reduced in the presence of a metallic catalyst such as Raney nickel in a hydrogen atmosphere or ammonia, whereby 3-(4-methoxyphenoxy)propylamine (compound (4)) can be produced.

In each reaction step carried out in the present invention, a target substance may be isolated through a routine purification method employed in organic synthesis chemistry such as filtration, washing, drying, re-crystallization, or chromatographic purification, in accordance with needs.

EXAMPLES

The present invention will next be described in more detail by way of examples.

Production Example 1

Synthesis of n-butyl (S)-2-trifluoromethanesulfonyloxybutyrate

[F7]

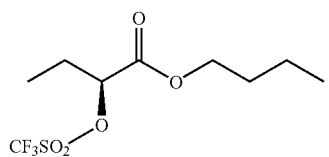

n-Butyl (S)-2-hydroxybutyrate (1.0 g, 99% ee) was dissolved in methylene chloride (8 mL), and pyridine (518 mg) was added at 0° C. to the resultant solution. Subsequently, trifluoromethanesulfonic anhydride (1.8 g) was added dropwise thereto at 0° C., and the mixture was stirred for 10 minutes. The reaction mixture was directly subjected to silica gel column chromatography, followed by passage of methylene chloride through the column. The eluate of interest was concentrated under reduced pressure, to thereby yield 1.8 g of a colorless, oily substance (98.2%).

$^1$H-NMR (400 MHz, CDCl$_3$) δ ppm: 0.93 (t, J=7 Hz, 3H), 1.05 (t, J=7 Hz, 3H), 1.34-1.43 (m, 2H), 1.65 (quintet, J=7 Hz, 3H), 1.97-2.08 (m, 2H), 4.23 (td, J=7.3 Hz, 2H), 5.06 (dd, J=7.5 Hz, 1H).

Example 1

Synthesis of n-butyl (R)-2-(3-formylphenoxy)butyrate

[F8]

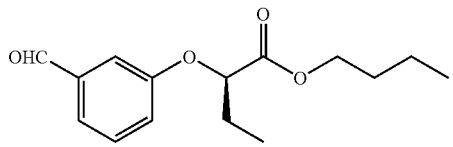

Potassium carbonate (473 mg) was added to a solution of 3-hydroxybenzaldehyde (418 mg) in acetonitrile (10 mL). Subsequently, n-butyl (S)-2-trifluoromethanesulfonyloxybutyrate (1.0 g) was added to the mixture, followed by stirring at room temperature for 12 hours. Ethyl acetate was added to the reaction mixture, and the resultant mixture was washed sequentially with water and saturated brine, followed by drying over sodium sulfate anhydrate. The reaction mixture was filtered, and the filtrate was concentrated under reduced pressure. The residue was purified through silica gel column chromatography (hexane/ethyl acetate=4/1), to thereby yield 904 mg of a colorless, oily substance (99.9%).

$^1$H-NMR (400 MHz, CDCl$_3$) δ ppm: 0.89 (t, J=7 Hz, 3H), 1.10 (t, J=7 Hz, 3H), 1.31 (sextet, J=7 Hz, 2H), 1.60 (quintet, J=7 Hz, 2H), 2.02 (quintet, J=7 Hz, 2H), 4.17 (t, J=7 Hz, 2H), 4.65 (t, J=6 Hz, 1H), 7.18-7.20 (m, 1H), 7.34-7.35 (m, 1H), 7.42-7.50 (m, 2H), 9.96 (s, 1H).

Production Example 2

Synthesis of 3-(4-methoxyphenoxy)propionitrile

[F9]

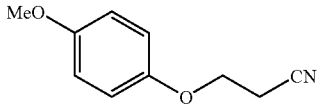

4-Methoxyphenol (263.0 g) was dissolved in acrylonitrile (224.8 g), and Triton B (18 mL) was added dropwise to the solution at room temperature, followed by stirring at 80° C. for 48 hours. The reaction mixture was cooled to room temperature under gentle stirring, and the mixture was further stirred for 12 hours. Subsequently, the mixture was left to stand at 6° C., to thereby allow precipitation of white prisms. After removal of the mother liquor through decantation, cold toluene (300 mL) was added, and crystals were collected through filtration. The thus-collected crude crystals were dried under reduced pressure at room temperature for 3 hours (crude crystals: 232.6 g). The crude crystals were dissolved in ethyl acetate (250 mL) at 50° C., and n-heptane (250 mL) was added slowly to the resultant solution under stirring. The crude crystals were recrystallized under gentle stirring for 12 hours. After removal of the mother liquor through decantation, n-heptane (300 mL) was added, and crystals were collected through filtration. The thus-collected crystals were washed with n-heptane (400 mL), and the crystals were dried under reduced pressure at room temperature (first crop of crystals: white prisms (154.5 g)). Since the mother liquor still produced crystals, they were collected as secondary crystals which were pale yellow prisms (second crop of crystals: pale yellow prisms (56.1 g)). Subsequently, all the filtrates and the n-heptane wash liquid were collected, and the combined mixture was concentrated under reduced pressure. Toluene (500 mL) was added to the residue, and the mixture was washed sequentially with 1N aqueous sodium hydroxide solution (100 mL×3), water (500 mL), 1N aqueous hydrochloric acid solution (100 mL×3), water (500 mL), and saturated brine (300 mL), followed by drying over sodium sulfate anhydrate for 30 minutes. After filtration, the filtrate was concentrated under reduced pressure. The residue was dissolved in ethyl acetate (150 mL) at 50° C., and n-heptane (150 mL) was slowly added to the resultant solution under stirring. The liquid was gently stirred for 12 hours for recrystallization. After removal of the mother liquor through decantation, n-heptane (200 mL) was added, and crystals were collected through filtration. The thus-collected crystals were washed with n-heptane (300 mL), followed by drying under reduced pressure at room temperature (third crop of crystals: white prisms (59.0 g)). In a similar manner, pale yellow prisms were collected as quaternary crystals (fourth crop of crystals: 19.0 g). The total amount of the four crystals was 288.6 g (yield: 76.9%), with crude crystals (yellow prisms) remaining (21.8 g, 5.8%).

$^1$H-NMR (400 MHz, CDCl$_3$) δ ppm: 2.79 (t, J=7 Hz, 2H), 3.77 (s, 3H), 4.15 (t, J=7 Hz, 2H), 6.85 (d, J=7 Hz, 4H).

Melting point: 64.4° C.

Production Example 3

Synthesis of 3-(4-methoxyphenoxy)propylamine

[F10]

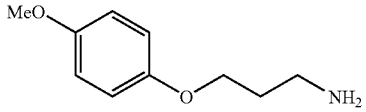

In an argon atmosphere, 3-(4-methoxyphenoxy)propionitrile (5.0 g) was dissolved in tetrahydrofuran (20 mL), and a borane-tetrahydrofuran complex (1.02 mol/L, 30.0 mL) was added dropwise to the resultant solution at 80° C. over 10 minutes. The mixture was stirred for 3 hours at 80° C. Thereafter, the reaction mixture was cooled to room temperature. Under cooling on ice, 4N aqueous sodium hydroxide solution (30 mL) was added thereto over 10 minutes. Ten minutes after, the mixture was stirred at room temperature for 5 minutes, and further stirred at 80° C. for 12 hours. The mixture was cooled to room temperature, and toluene (100 mL) was added thereto, followed by stirring for 1 hour. Subsequently, after removal of insoluble matter through filtration by means of Celite, the organic layer was collected and washed sequentially with water (100 mL×2) and saturated brine (100 mL), followed by drying over sodium sulfate anhydrate (80 g). After filtration, the filtrate was concentrated under reduced pressure, to thereby yield 4.0 g of a white solid (79.0%).

$^1$H-NMR (400 MHz, CD$_3$OD) δ ppm: 2.05 (quintet, J=7 Hz, 2H), 3.07 (t, J=7 Hz, 2H), 3.71 (s, 3H), 4.01 (t, J=6 Hz, 2H), 6.79-6.85 (m, 4H).

Referential Example 1

Synthesis of n-butyl (R)-2-[3-[N-[3-(4-methoxyphenoxy)propyl]aminomethyl]phenoxy]butyrate

[F11]

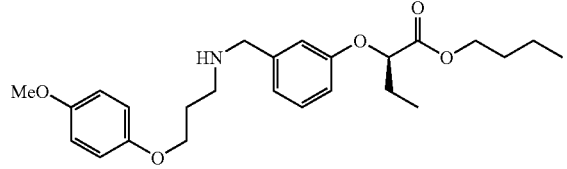

3-(4-Methoxyphenoxy)propylamine (34 mg) was dissolved in methanol (3 mL), and a solution (2 mL) of n-butyl (R)-2-(3-formylphenoxy)butyrate (50 mg) in methanol was added thereto under stirring at room temperature. The mixture was further stirred at 80° C. for 12 hours. Subsequently, an aqueous solution (0.5 mL) of sodium borohydride (7 mg) was added to the solution at room temperature, and the mixture was stirred for 30 minutes. The reaction solution was concentrated under reduced pressure, and chloroform was added to the concentrated product. The formed organic layer was washed with water. The washed organic layer was dried over sodium sulfate anhydrate, and concentrated under reduced pressure, to thereby yield 81 mg of a pale yellow, oily substance. The entirety of the substance was employed in the following reaction without any further treatment.

¹H-NMR (400 MHz, CDCl₃) δ ppm: 0.87 (t, J=7 Hz, 3H), 1.07 (t, J=7 Hz, 3H), 1.29 (sextet, J=7 Hz, 2H), 1.60 (quintet, J=7 Hz, 2H), 1.91-2.01 (m, 5H), 2.79 (t, J=7 Hz, 2H), 3.75 (s, 3H), 3.76 (s, 2H), 3.98 (t, J=6 Hz, 2H), 4.00-4.19 (m, 2H), 4.56 (t, J=6 Hz, 1H), 6.75 (dd, J=8.2 Hz, 1H), 6.79-6.85 (m, 4H), 6.88-6.95 (m, 2H), 7.20 (t, J=8 Hz, 1H).

Referential Example 2

Synthesis of n-butyl (R)-2-[3-[[N-(benzoxazol-2-yl)-N-3-(4-methoxyphenoxy)propyl]aminomethyl]phenoxy]butyrate

[F12]

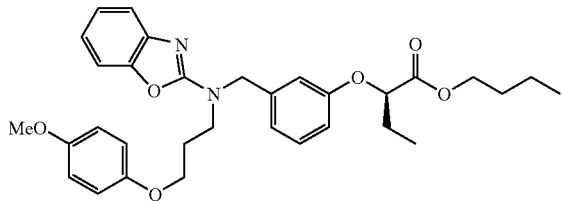

n-Butyl (R)-2-[3-[N-[3-(4-methoxyphenoxy)propyl]aminomethyl]phenoxy]butyrate (81 mg) was dissolved in acetonitrile (5 mL), and triethylamine (29 mg) was added dropwise to the ester solution at room temperature. Subsequently, 2-chlorobenzoxazol (35 mg) was added thereto, followed by stirring at 80° C. for 12 hours. Water was added to the mixture, and the resultant mixture was extracted with ethyl acetate. The formed organic layer was washed with saturated brine, and the washed organic layer was dried over sodium sulfate anhydrate and concentrated under reduced pressure. The residue was purified through silica gel chromatography (hexane/ethyl acetate=5/2), to thereby yield 83 mg of a colorless, oily substance (81%).

¹H-NMR (400 MHz, CDCl₃) δ ppm: 0.83 (t, J=7.3 Hz, 3H), 1.03 (t, J=7.3 Hz, 3H), 1.18-1.29 (m, 2H), 1.44-1.55 (m, 2H), 1.93 (quintet, J=7.3 Hz, 2H), 2.12 (quintet, J=6.5 Hz, 2H), 3.67 (t, J=7.1 Hz, 2H), 3.74 (s, 3H), 3.94 (t, J=6.0 Hz, 2H), 3.98-4.13 (m, 2H), 4.51 (t, J=6.2 Hz, 1H), 4.72 (t, J=3.2 Hz, 2H), 6.74 (dd, J=8.3, 2.0 Hz, 1H), 6.78 (s, 4H), 6.84 (t, J=2.0 Hz, 1H), 6.88 (d, J=7.6 Hz, 1H), 6.99 (td, J=7.8, 1.2 Hz, 1H), 7.14 (td, J=7.8, 1.2 Hz, 2H), 7.19-7.24 (m, 3H), 7.34 (dd, J=7.8, 0.6 Hz, 1H).

Referential Example 3

Synthesis of (R)-2-[3-[[N-(benzoxazol-2-yl)-N-3-(4-methoxyphenoxy)propyl]aminomethyl]phenoxy]butyric acid

[F13]

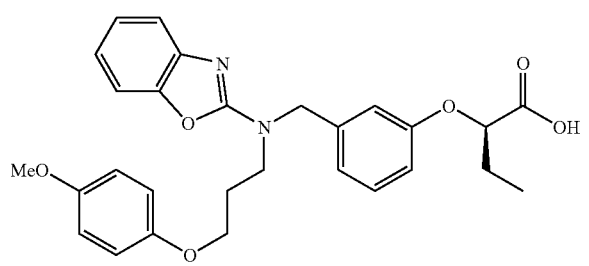

n-Butyl (R)-2-[3-[[N-(benzoxazol-2-yl)-N-3-(4-methoxyphenoxy)propyl]aminomethyl]phenoxy]butyrate (83 mg) was dissolved in ethanol (3 mL), and a 4N aqueous sodium hydroxide solution (0.1 mL) was added dropwise to the ester solution. The mixture was stirred at room temperature for 1 hour and concentrated under reduced pressure. Subsequently, a 1N aqueous sodium hydroxide solution was added thereto, followed by washing with diethyl ether. Thereafter, 1N hydrochloric acid was added to the formed aqueous layer so that the pH of the layer was adjusted to 1, and the layer was extracted with chloroform. The formed organic layer was dried over sodium sulfate anhydrate, and concentrated under reduced pressure. The residue was purified through preparative chromatography (chloroform/methanol=10/1), to thereby yield 72 mg of a colorless solid substance (96.1%).

¹H-NMR (400 MHz, CD₃OD) δ ppm: 0.94 (t, J=7.4 Hz, 3H), 1.81 (m, 2H), 1.99 (quintet, J=6.1 Hz, 2H), 3.60 (t, J=6.8 Hz, 2H), 3.61 (s, 3H), 3.85 (t, J=5.9 Hz, 2H), 4.40 (t, J=5.9 Hz, 1H), 4.65 (s, 2H), 6.69-6.80 (m, 7H), 6.91 (dt, J=7.2, 1.0 Hz, 1H), 7.05 (dt, J=7.2, 1.2 Hz, 1H), 7.12-7.18 (m, 4H).

Optical purity: 99% ee

Measurement conditions: HPLC
  Column: CHIRALCEL OD
  Solvent: hexane/isopropyl alcohol/trifluoroacetic acid=60/40/0.1
  Flow rate: 1 mL/min
  Retention time: R-form; 13.3 min (S-form; 7.9 min)

Through the above synthetic route, compound (A-1) (Referential Example 3 compound), which is a PPAR-activating compound, was successfully produced at a high optical purity (99% ee) from n-butyl (S)-2-hydroxybutyrate (99% ee) serving as a starting material. Namely, optical purity of n-butyl (S)-2-hydroxybutyrate is maintained at high level through the aforementioned reaction steps, clearly indicating that, through the method of the present invention, Example 1 compound, which is a production intermediate for compound (A-1), can be produced at high yield and high optical purity.

The invention claimed is:
1. A method for producing an optically active benzaldehyde derivative represented by formula (3):
[F3]

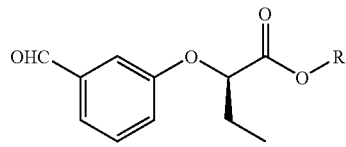

(3)

(wherein R represents a C1 to C6 alkyl group or a C7 to C8 aralkyl group), characterized in that the method comprises reacting 3-hydroxybenzaldehyde represented by formula (1):
[F1]

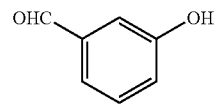

(1)

with an optically active 2-trifluoromethanesulfonyloxy-butyric acid ester represented by formula (2):

[F2]
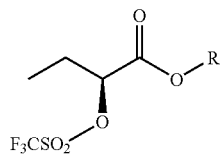
(2)
(wherein R has the same meaning as defined above) in the presence of a base.
2. An optically active benzaldehyde derivative represented by formula (3):
[F4]
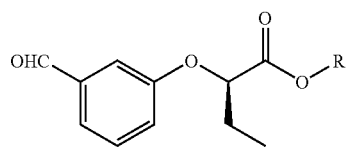
(3)
(wherein R represents a C1 to C6 alkyl group or a C7 to C8 aralkyl group).
* * * * *